United States Patent [19]

Otani et al.

[11] Patent Number: 5,730,135
[45] Date of Patent: Mar. 24, 1998

[54] ULTRASONIC BONE DIAGNOSTIC APPARATUS AND METHOD

[75] Inventors: Takahiko Otani, Kyoto; Atsushi Hosokawa, Maizuru; Takuji Suzaki; Haruyoshi Hirata, both of Miyanohigashi-machi, all of Japan

[73] Assignee: Horiba, Ltd., Kyoto, Japan

[21] Appl. No.: 709,519

[22] Filed: Sep. 6, 1996

[30] Foreign Application Priority Data

Sep. 12, 1995 [JP] Japan ................. 7-260864
Dec. 29, 1995 [JP] Japan ................. 7-354452

[51] Int. Cl.⁶ ........................................ A61B 8/00
[52] U.S. Cl. ...................................... 128/661.03
[58] Field of Search ............... 128/660.01, 660.02, 128/660.06, 661.03

[56] References Cited

U.S. PATENT DOCUMENTS

| 4,913,157 | 4/1990 | Pratt, Jr. et al. ............ 128/661.03 |
| 4,941,474 | 7/1990 | Pratt, Jr. et al. ............ 128/660.06 |
| 5,143,069 | 9/1992 | Kwon et al. ............. 128/660.06 X |
| 5,259,384 | 11/1993 | Kaufman et al. ........... 128/660.06 X |
| 5,349,959 | 9/1994 | Wiener et al. ............. 128/660.06 |
| 5,396,891 | 3/1995 | Whitney et al. ............. 128/661.03 |
| 5,426,979 | 6/1995 | Kantorovich et al. ......... 128/660.01 X |
| 5,433,203 | 7/1995 | Kimyera et al. ........... 128/660.06 |
| 5,452,722 | 9/1995 | Langton .................. 128/661.03 X |

*Primary Examiner*—Francis Jaworski
*Attorney, Agent, or Firm*—Price, Gess & Ubell

[57] ABSTRACT

An ultrasonic diagnostic method and apparatus is provided wherein an ultrasonic wave is transmitted through a patient to contact the human bone and the corresponding diagnostic waveform is then compared with a standard prestored waveform of a comparable healthy bone. The patient's bone is then judged to determine the osteoporosis condition of the patient.

17 Claims, 15 Drawing Sheets

ULTRASONIC BONE DIAGNOSTIC APPARATUS AND METHOD

BACKGROUND OF THE INVENTION

1. Field of the Invention

The present invention relates to an ultrasonic bone diagnostic method and apparatus for obtaining information about bone properties (bone weight, bone strength, etc.).

2. Description of Related Art

Conventional techniques for diagnosing bone properties in humans include the following:

(1) Double energy X-ray absorption method (DEXA or DXA) of emitting and penetrating X-rays through bones, measuring the X-ray absorption in bones to determine the bone surface density, and relating with the degree of fracture due to osteoporosis when the bone surface density is small, which means small bone weight and hence likeliness of fracture; and (2) Method of emitting and penetrating ultrasonic waves through the calcaneus or patella, determining the propagation speed of ultrasonic waves in the bone and the damping factor of an ultrasonic signal after penetration from the time required for penetration of the ultrasonic waves at this time, estimating the Young's modulus of the bone from the propagation speed, and relating it with the bone strength. The bone weight is estimated from a bone surface density determined by other DEXA diagnostic apparatus, with a damping factor regarded to depend on the bone beam structure of spongy bone. Also using the values of propagation speed and damping factor, it has also been attempted to determine a bone hardness index called stiffness.

However, the DEXA diagnostic apparatus used in the technique (1) is large and expensive, and this technique also involves a potential problem of X-ray exposure. The technique (2) has been hitherto proposed, but it is not generally high in precision and is not used widely, and the ultrasonic diagnostic apparatus used in this ultrasonic method is still being studied in correlation with the DEXA diagnostic apparatus. Therefore, conventionally, in diagnosis of bones, mainly, the bone weight (bone surface density) was measured, and the information obtained by the ultrasonic diagnostic apparatus was used on the basis of reliability when compared with a value measured by the DEXA diagnostic apparatus.

Therefore, to examine the bone of a patient, it was difficult to obtain the necessary information about the bone weight and bone strength simultaneously, to predict the specific bone structure to see if the bone is simplified or not, or to judge the amount of bone. The prior art is still seeking an improved method and apparatus for measuring a patient's bones.

OBJECTS AND SUMMARY OF THE INVENTION

The present invention is devised to solve the problems of the prior art, including the use of large and expensive apparatus, X-ray exposure in X-ray diagnostic apparatus, and unclear properties of bone expressed by the ultrasonic diagnostic apparatus.

It is an object of the present invention to provide an ultrasonic bone diagnostic method capable of simplifying the process of judging bone properties such as bone weight and bone strength, thereby enhancing the reliability of the diagnostic procedure.

The invention is characterized by emitting ultrasonic waves to human bones including spongy (cancellous) bone at a measuring position, penetrating through the bone, receiving the transmitted waves as diagnostic waveforms, and comparing the diagnostic waves with standard waveforms.

In a first aspect of the invention, an ultrasonic wave emitted from a transmit transducer is caused to enter and penetrate through a human bone including spongy bone as the measuring position, the transmitted wave is received in a receive transducer, a resulting diagnostic waveform at this time is compared with a standard waveform, and the diagnostic state of the human bone is judged depending on the difference or absence of difference from the comparison.

In a second aspect of the invention, an ultrasonic wave emitted from a transmit transducer is entered and penetrated through a human bone including spongy bone as the measuring position, the transmitted wave is received in a receive transducer, a resulting diagnostic waveform at this time is processed by a computer, and is compared with a similarly processed standard waveform, and the state of the human bone is judged depending on the presence or absence of difference with the standard waveform characteristics.

Herein, the standard waveform has the following waveform characteristics. That is, the waveform after transmitting an ultrasonic wave through the human bone including spongy bone is small in fluctuation in healthy subjects, but considering a certain difference depending on the race and region of the patient, plural waveforms are obtained from the object population, and added and averaged, and a waveform as normal as possible is obtained. Furthermore precise diagnosis may be done using individual standard waveforms obtained from each sex and age population.

Examples of human bone including spongy bone are, among others, the radius of forearm, patella, calcaneus, femoral cervix, and lumbar vertebra.

As the ultrasonic waveform, a waveform of short pulse form is preferred because the response is relatively simple and it is easy to judge the waveform.

In the first aspect of the invention, comparison items between the standard waveform and diagnostic waveform include the following:

(1) Zero cross number or pulse width in a range of a time interval including a first wave and a second wave of both waveforms;

(2) Magnitude of amplitude of peaks of both waveforms or amplitude ratio of a first wave and a second wave;

(3) Number of peaks in a range of time interval including first wave and second wave of both waveforms; and (4) Maximum value or pattern in correlative function of both waveforms.

Herein, the first wave and second wave refer to the waves indicated by I and II in, for example, FIG. 4 or FIG. 6, and they are the first and second reaching waves.

One of the waveform processing methods by computer in a second aspect of the invention is a frequency analysis such as Fast Fourier Transformation (FFT). It may be also possible to judge the degree of progress of osteoporosis such as bone structure and strength on the basis of the frequency of amplitude of transmitted wave after waveform processing by computer or frequency analysis processing. Instead of the frequency of amplitude of the transmitted wave, the same judgment may be also made on the basis of the frequency characteristic of phase.

Moreover, concerning the frequency characteristic of amplitude of the transmitted wave and frequency characteristic of phase of the transmitted wave, the same judgment may be made by a two-dimensional plotting of phase and amplitude of the data at a frequency showing a difference between a healthy subject data and patient data.

In the case of measurement, it is preferred not to include air between the measuring position and the transmit transducer and receive transducer, and, for example, the following methods are recommended:

a. The measuring position is kept in contact with an elastic bolus filled with water or adjusting solution which includes water and glycerin, and is brought into contact with the transmit transducer and receive transducer.

b. The measuring position is coated with gel (or jelly) matter, and is brought into contact, in this state, with the transmit transducer and receive transducer.

c. The measuring position is kept in contact with polymer containing water, silicone pad or the like, and is brought into contact with the transmit transducer and receive transducer.

d. The measuring position is put in water in which the transmit transducer and receive transducer are installed preliminarily.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DETAILED DESCRIPTION OF THE PREFERRED EMBODIMENTS

Figure 1:
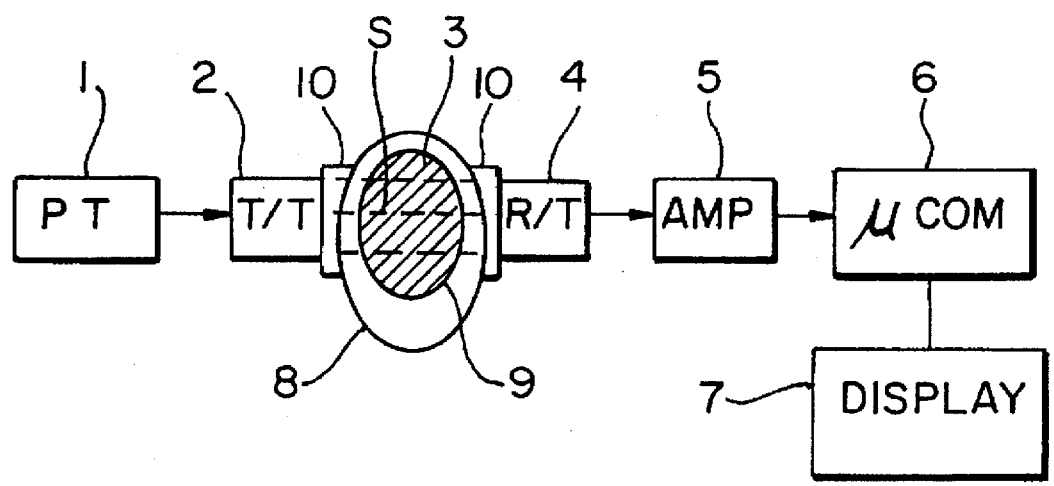
FIG. 1 is a schematic diagram of an apparatus for executing an ultrasonic bone diagnostic method of the present invention.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an ultrasonic bone diagnostic method and apparatus.

Referring now to the drawings, preferred embodiments are described in detail below.

FIG. 1 shows an example of a schematic diagram of an apparatus for realizing an ultrasonic bone diagnostic method of the present invention. In the diagram, reference numeral 1 denotes a pulse transmitter, which may also include a pulse amplifier. Reference numeral 2 is a transmit transducer for receiving a pulse output from the pulse transmitter 1 and emitting a pulse ultrasonic wave S of narrow pulse width to an object 3, and 4 is a receive transducer for receiving a transmitted wave penetrating through the object 3. Reference numeral 5 is a signal amplifier for appropriately amplifying the output of the receive transducer 4, 6 is a computer as an operation processor for processing and calculating a transmitted waveform, and 7 is a display unit.

Herein, as the ultrasonic wave S, a wave containing many frequency components below 5 MHz, such as a pulse wave with a broad bandwidth having an appropriate waveform is selected. As the object 3, a bone including spongy bone is preferred, and preferred examples are radius of forearm, patella, calcaneus, femoral cervix, and lumbar vertebra, and in the following description, the radius is used as the object 3. Hence, reference numeral 8 is the forearm, and 9 is the peripheral soft tissues of the radius 3.

When measuring the bone of a patient by using a measuring apparatus having such a structure, the forearm abutting portion of the transmit transducer 2 and the forearm abutting portion of the receive transducer 4 are not brought into direct contact with the measuring position of the forearm (a proper position between the wrist and elbow in which the radius 3 is located), but an acoustic impedance adjuster 10 filled with water or adjusting solution properly mixing water and glycerin in an elastic bolus is detachably fitted to the forearm abutting portion, and the acoustic impedance adjuster 10 is tightly fitted to the measuring position. It is also preferred not to permit air to extend between the measuring position and the transmit transducer 2 and receive transducer 4.

The reason is as follows. That is, if an air layer is formed between the measuring position and the transmit transducer 2 and receive transducer 4 at the time of measurement, when the ultrasonic wave S enters the forearm 8 through the air layer, or when the ultrasonic wave (transmitted wave) entering the forearm 8 and penetrating through the radius 3 goes out to the air layer through the forearm 8, an acoustic impedance varies in the boundary between the forearm 8 and air layer, in such area the ultrasonic wave S is reflected, and a reflected signal may be mixed into the signal received by the receive transducer 4, or the signal may be extremely attenuated, which may become a disturbing wave to adversely affect the precision of measurement.

As a technique for eliminating effects of changes of the acoustic impedance, aside from the acoustic impedance adjuster 10, gel (or jelly) matter may be applied on the measuring position to contact with the transmit transducer 2 and receive transducer 4 in that state, or the measuring position may be kept in contact with a polymer containing water or silicone pad, and is made to contact with the transmit transducer 2 and receive transducer 4, or the measuring position may be put in water in which the transmit transducer 2 and receive transducer 4 are installed preliminarily. These techniques are further disclosed in a Japanese patent application filed in Japan by the present Applicants on Apr. 11, 1995 ("Method and Apparatus of Ultrasonic Bone Diagnosis," Japanese Patent Application No. Hei. 7-111302).

To examine a bone by using a diagnostic apparatus of the present invention, the forearm 8 is placed between the transmit transducer 2 and receive transducer 4, and the acoustic impedance adjusters 10 provided in the forearm abutting portions of the transmit transducer 2 and receive transducer 4 are brought into tight contact with the measuring position of the forearm 8. In this state, a pulse ultrasonic wave Sof, for example, of a frequency of 5 MHz or less is emitted from the transmit transducer 2. This ultrasonic wave S enters the forearm 8 through the acoustic impedance adjuster 10 of the transmit transducer 2 side, and penetrates through the radius 3 through the soft tissues 9, and the transmitted wave is sent out of the forearm 8 through the soft tissues 9, and is further received by the receive transducer 4 through the acoustic impedance adjuster 10 of the receive transducer 4 side.

The transmitted wave signal received by the receive transducer 4 is amplified to a required amplitude by the signal amplifier 5, and is taken into the computer 6. In the computer, waveform processing and operation are executed by proper techniques, and the values expressing the properties of the object, the radius 3, for example, the bone weight in the spongy bone and/or bone quality are obtained, and the presence or absence of osteoporosis is determined, and it is displayed in the screen of the display unit 7 or stored in a proper memory device (not shown).

Examples of waveform processing and operation by the computer 6 are described below specifically by referring to the drawings in FIG. 2 and subsequent figures.

First, using the diagnostic apparatus, plural healthy subjects are examined, and standard waveforms are prepared. That is, an ultrasonic wave S is emitted to the radius 3 of a healthy subject, and the transmitted wave is received by the receive transducer 4, and the plural waveforms obtained at this time are added and averaged, and a standard waveform is prepared.

Figure 2:
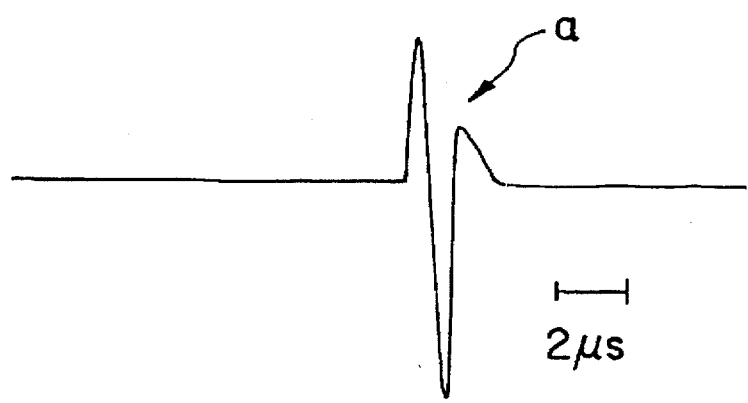
FIG. 2 is a waveform diagram showing an example of ultrasonic waveform used in the diagnostic method.
Figure 3:
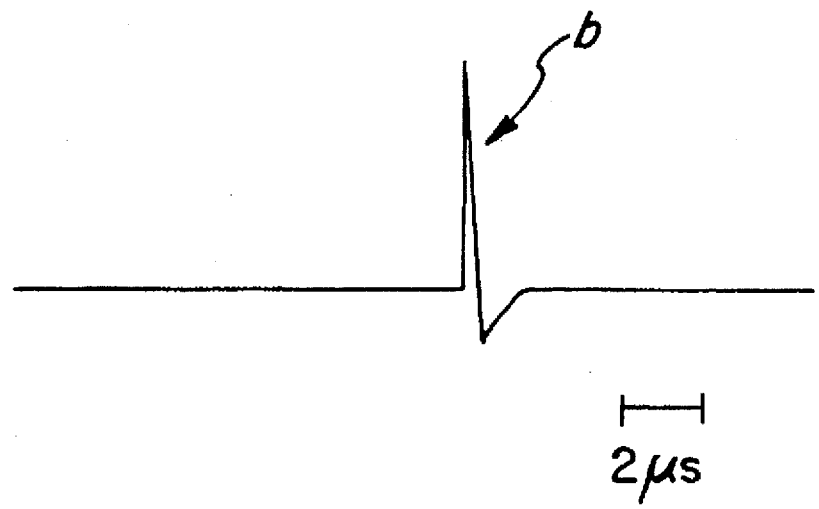
FIG. 3 is a waveform diagram showing other example of ultrasonic waveform used in the diagnostic method.

FIG. 2 and FIG. 3 show examples of waveforms of ultrasonic wave S entering the radius 3, and waveform a in FIG. 2 is generated by applying a voltage of raised cosine wave, and waveform b in FIG. 3 is generated by applying a voltage of a step wave.

Figure 4:
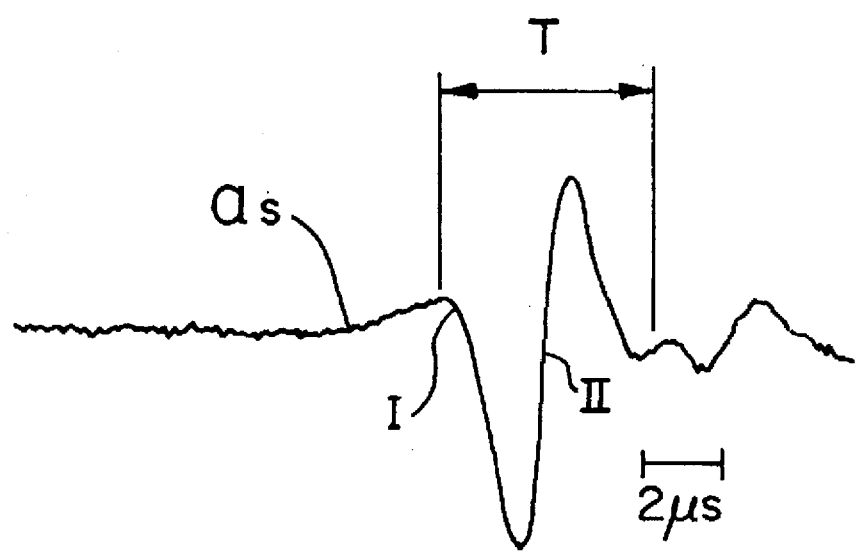
FIG. 4 is a waveform diagram showing an example of a standard waveform used in the diagnostic method.
Figure 5:
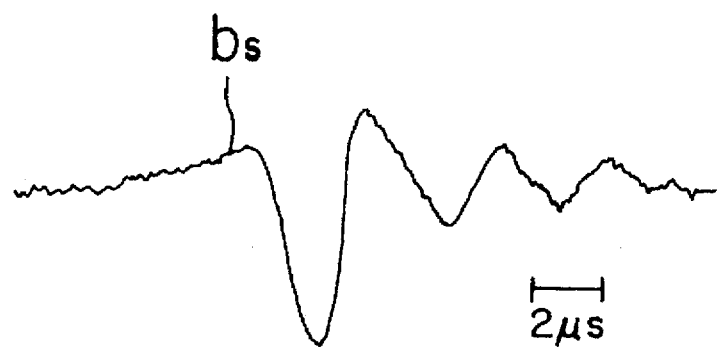
FIG. 5 is a waveform diagram showing another example of a standard waveform used in the diagnostic method.
Figure 6:
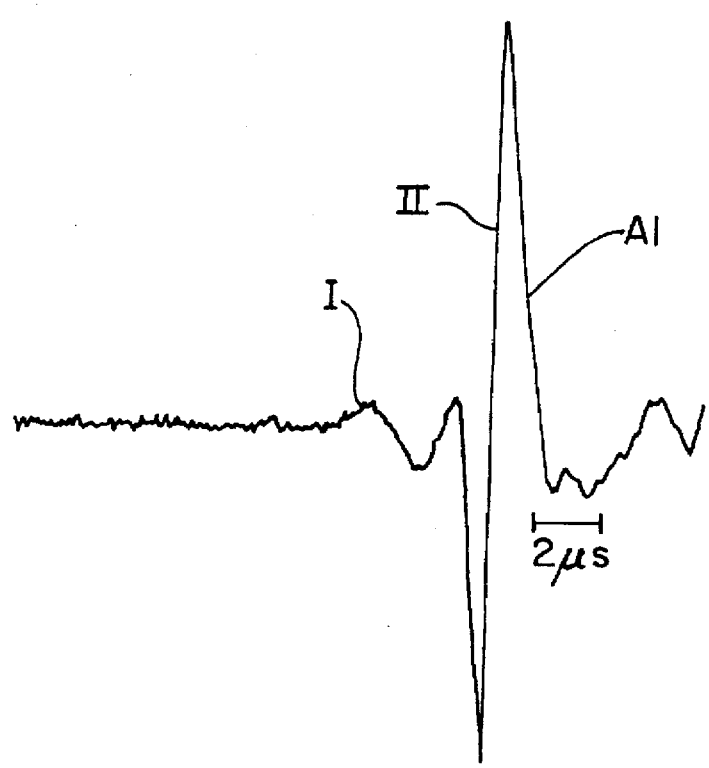
FIG. 6 is a diagram showing an example of a diagnostic waveform.
Figure 7:
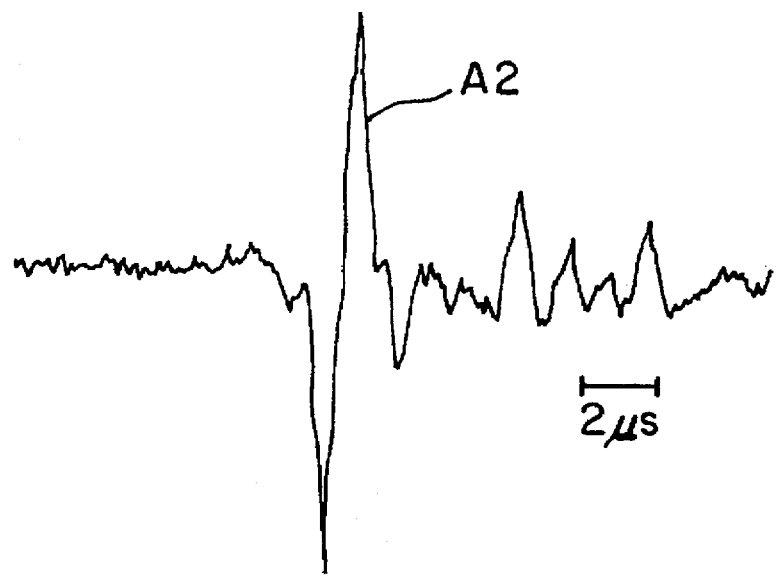
FIG. 7 is a diagram showing an example of a diagnostic waveform.
Figure 8:
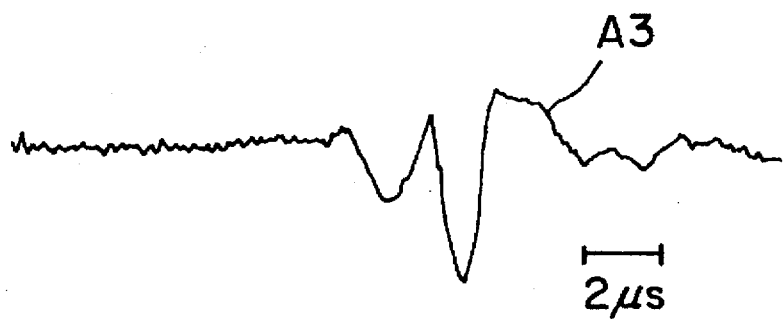
FIG. 8 is a diagram showing an example of a diagnostic waveform.
Figure 9:
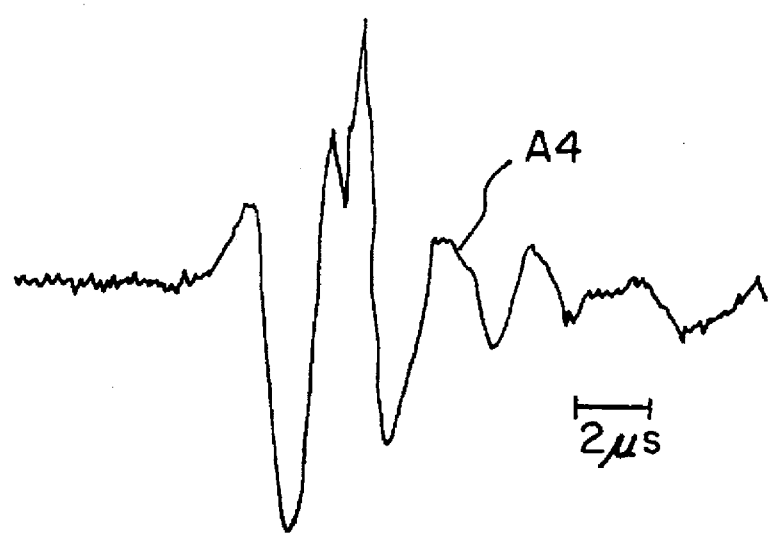
FIG. 9 is a diagram showing an example of a diagnostic waveform.
Figure 10:
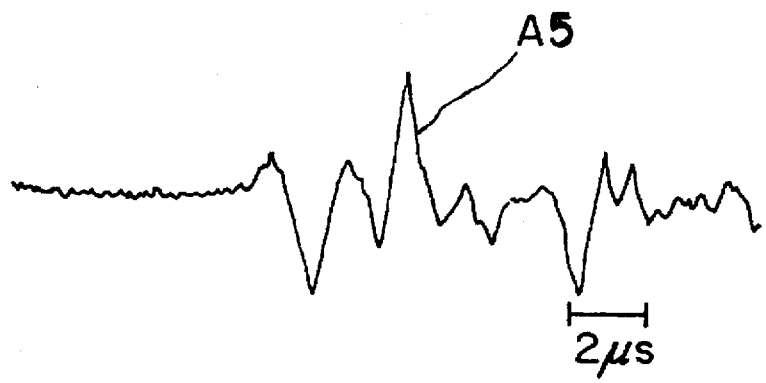
FIG. 10 is a diagram showing an example of a diagnostic waveform.
Figure 11:
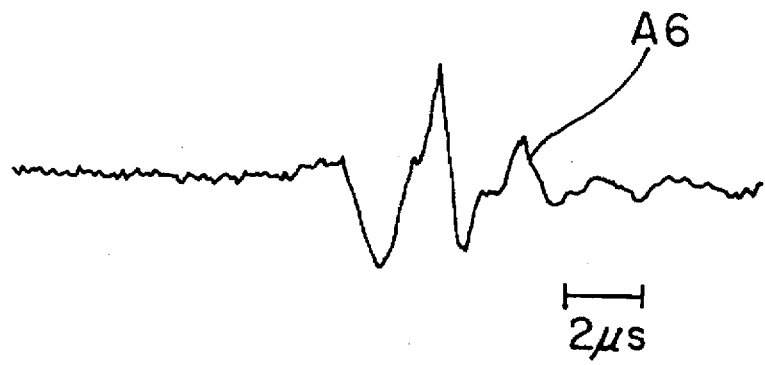
FIG. 11 is a diagram showing an example of a diagnostic waveform.
Figure 12:
FIG. 12 is a diagram showing an example of a diagnostic waveform.
Figure 13:
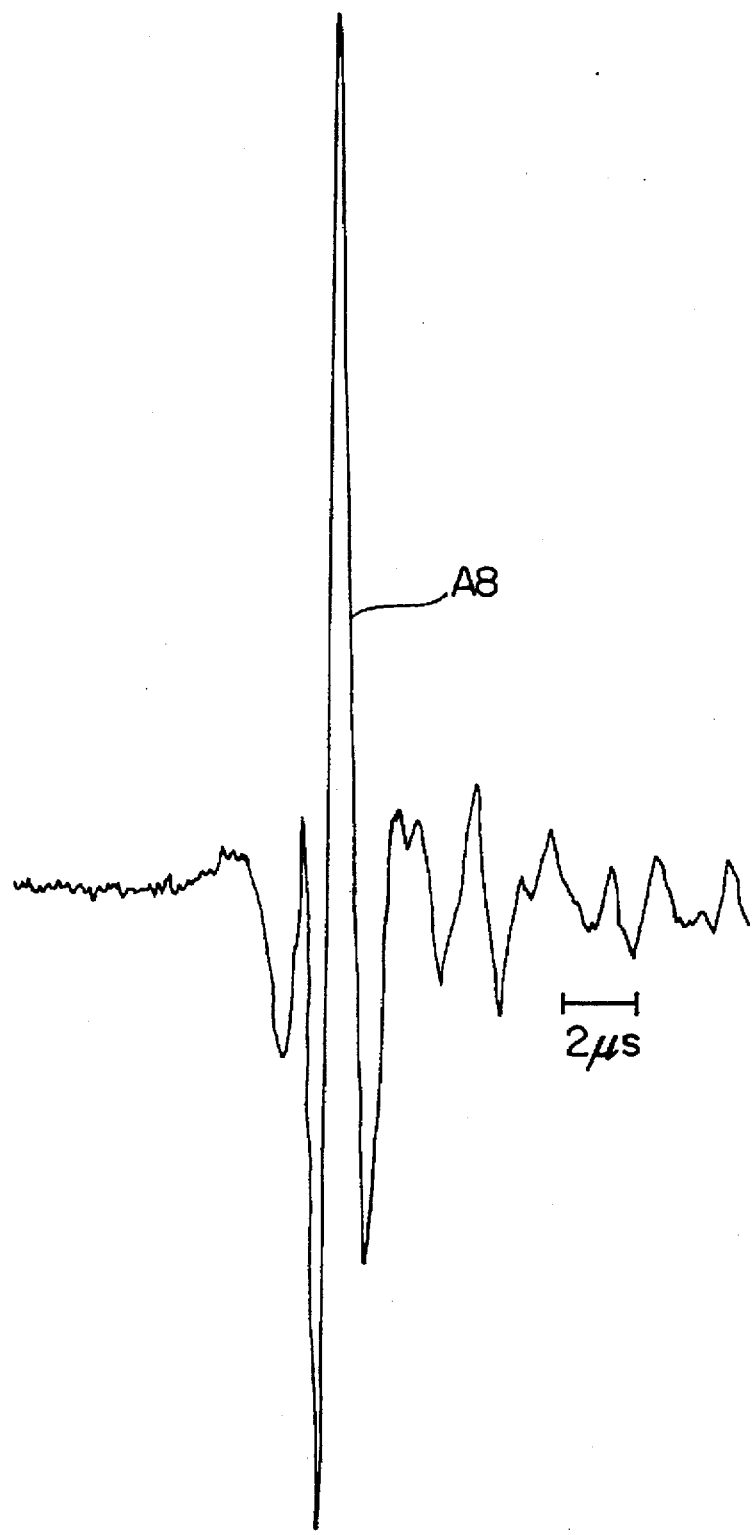
FIG. 13 is a diagram showing an example of a diagnostic waveform.
Figure 14:
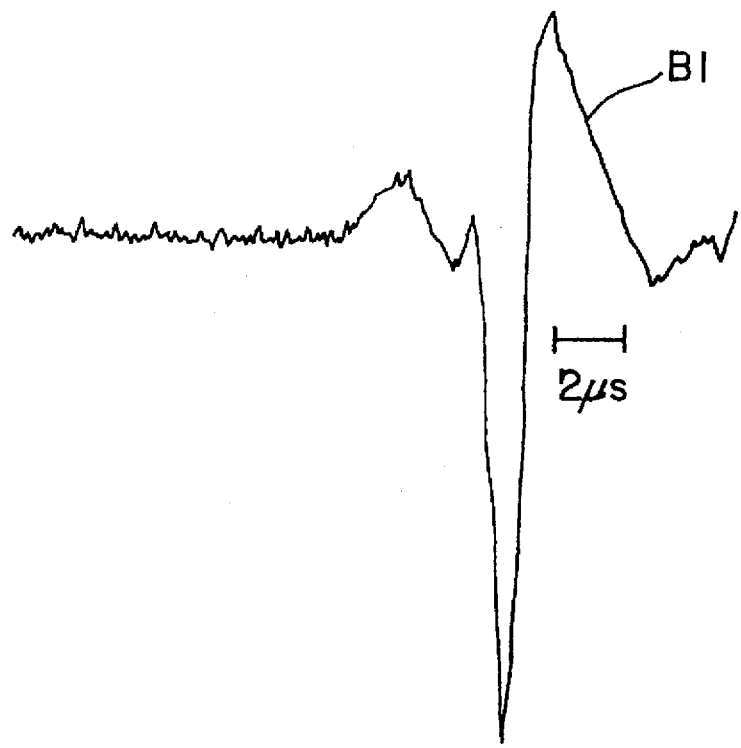
FIG. 14 is a diagram showing an example of a diagnostic waveform.
Figure 15:
FIG. 15 is a diagram showing an example of a diagnostic waveform.
Figure 16:
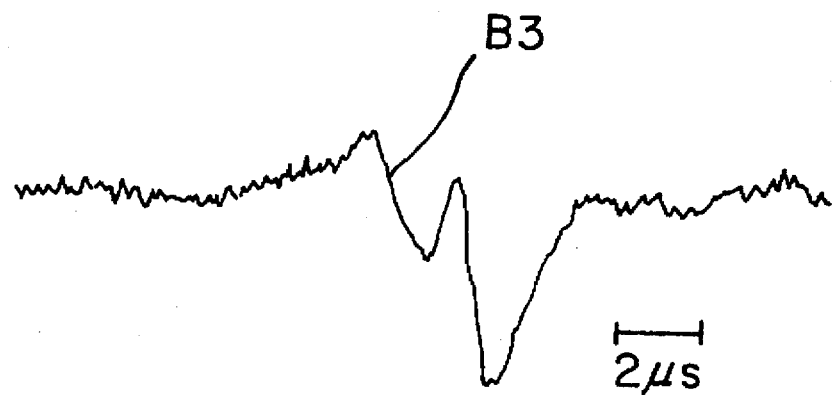
FIG. 16 is a diagram showing an example of a diagnostic waveform.
Figure 17:
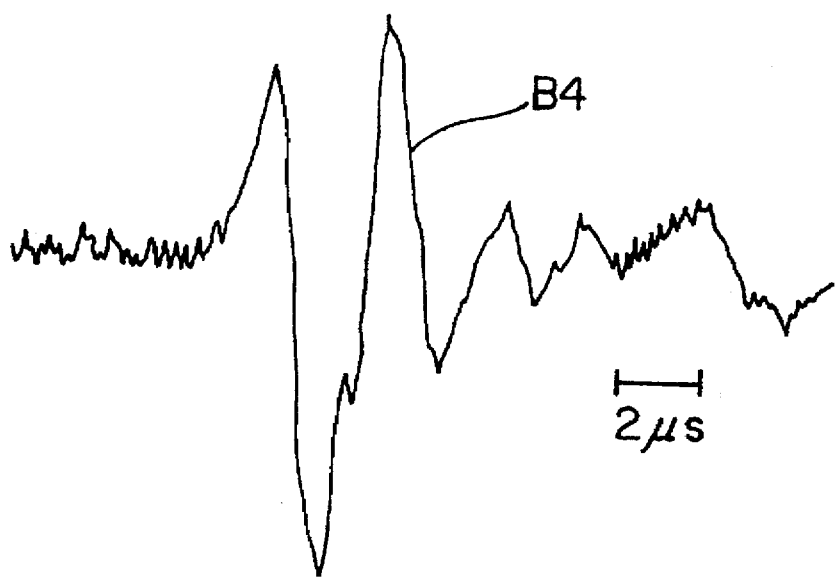
FIG. 17 is a diagram showing an example of a diagnostic waveform.
Figure 18:
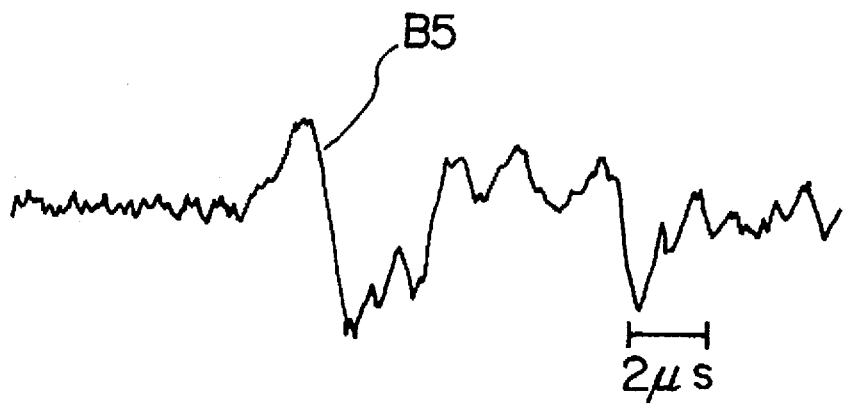
FIG. 18 is a diagram showing an example of a diagnostic waveform.
Figure 19:
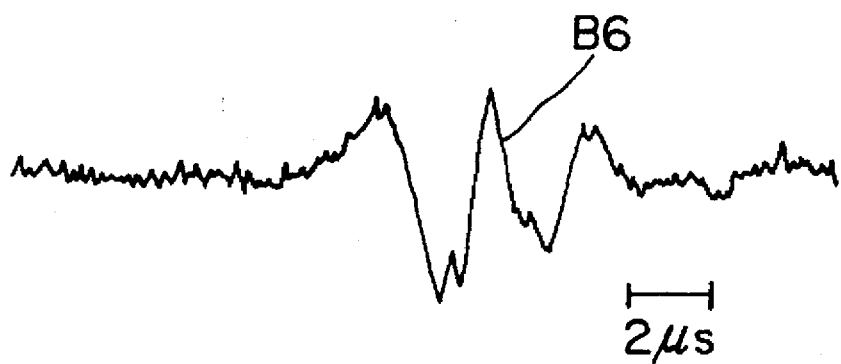
FIG. 19 is a diagram showing an example of a diagnostic waveform.
Figure 20:
FIG. 20 is a diagram showing an example of a diagnostic waveform.
Figure 21:
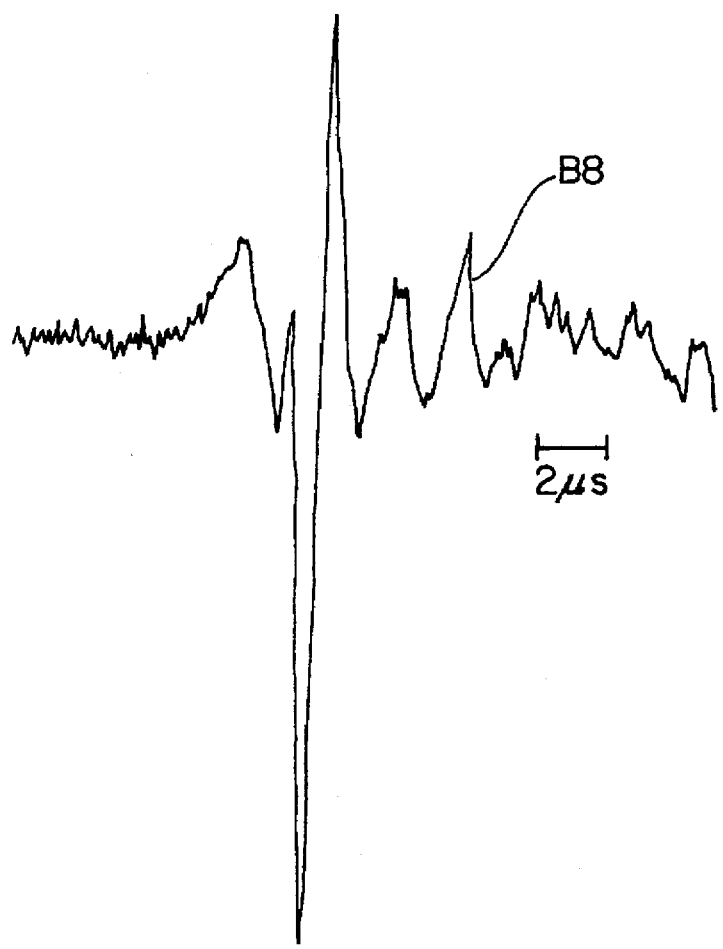
FIG. 21 is a diagram showing an example of a diagnostic waveform.

FIG. 4 and FIG. 5 are standard waves $a_s$, $b_s$ prepared by adding and averaging the waveforms obtained by putting waveform a and waveform b into the radius 3 of a 22-year-old man and a 23-year-old man, respectively.

In actual examination, by putting the ultrasonic wave S into the radius 3 of the subject, the diagnostic waveform obtained at this time is compared with the standard waveform $a_s$ or $b_s$. In this case, the comparison is not limited to comparison of shape of the both waveforms, but can include the following:

(1) zero cross number or pulse width in a range of time interval including the first wave and second wave of both waveforms, (2) magnitude of amplitude of peaks of both waves or amplitude ratio of first wave and second wave, (3) number of peaks in a range of time interval including the first wave and second wave of both waveforms, and (4) maximum value or pattern in the correlative function of both waveforms are also compared, and depending on the presence or absence of difference and magnitude of difference, the bone condition of the subject is evaluated.

In eight female subjects (55 to 75 years of age), waveform a and waveform b were emitted, and diagnostic waveforms were obtained. FIG. 6 to FIG. 13 show diagnostic waveforms obtained in the case of waveform a, which are indicated by reference numerals A1 to A8. FIG. 14 to FIG. 21 are diagnostic waveforms obtained in the case of waveform b, which are indicated by reference numerals B1 to B8. That is, FIG. 6 (A1) and FIG. 14 (B1) show the diagnostic waveforms of a same subject, and similarly FIG. 7 (A2) and FIG. 15 (B2), FIG. 8 (A3) and FIG. 16 (B3), FIG. 9 (A4) and FIG. 17 (B4), FIG. 10 (A5) and FIG. 18 (B5), FIG. 11 (A6) and FIG. 19 (B6), FIG. 12 (A7) and FIG. 20 (B7), and FIG. 13 (A8) and FIG. 21 (B8) show diagnostic waveforms of a same subject, respectively.

In the standard waveforms $a_s$ and $b_s$, and diagnostic waveforms A1 to A8, B1 to B8, the number of peaks (or bottoms) was counted in a certain time (length) from the first peak. For example, as shown in FIG. 4, the number of peaks in a certain time T (for example, a range of 5 μsec) from the first peak is counted, and it is four in the standard waveform $a_s$ shown in FIG. 4. The waveforms in FIG. 5 to FIG. 21 were similarly counted, of which results are shown in Table 1 and Table 2.

TABLE 1

| Standard waveform $a_s$ | No. of Peaks |
| --- | --- |
|  | 4 |
| Waveform A1 | 5 |
| A2 | 11 |
| A3 | 5 |
| A4 | 6 |
| A5 | 6 |
| A6 | 8 |
| A7 | 7 |
| A8 | 9 |

TABLE 2

| Standard waveform $b_s$ | No. of Peaks |
| --- | --- |
|  | 3 |
| Waveform B1 | 5 |
| B2 | 6 |
| B3 | 6 |
| B4 | 6 |
| B5 | 8 |
| B6 | 8 |
| B7 | 7 |
| B8 | 8 |

In Table 1 and Table 2, waveforms A1 to A8, B1 to B8 are obtained from eight female subjects, and all these subjects are patients with osteoporosis diagnosed separately by the DEXA.

Table 1 shows the results of using waveform a as an oscillating wave, the number of peaks is four in the standard waveform $a_s$ of the healthy subject, whereas it is larger than four, ranging from five to eleven, in the waveforms A1 to A8 of the patients. In Table 2 showing the results of using waveform b as an oscillating wave, the number of peaks is three in the standard waveform b, of the healthy subject, whereas it is larger than three, ranging from five to eight, in the waveforms B1 to B8 of the patients.

That is, by comparing the number of peaks in a specific time period in the diagnostic waveform with the number of peaks in a same time period in the standard waveform, the condition of a bone of the subject may be evaluated, and whether osteoporosis or not can be judged, and moreover it is possible to predict whether the bone structure is simplified or not.

Incidentally, the greater the number of peaks in a specific time, the narrower is the width in the peak or bottom. That is, instead of counting the number of peaks, it is the same to compare the pulse width in a specific time period.

Alternatively, the magnitude of amplitude of peaks in the standard waveform and diagnostic waveform, or the amplitude ratio of the first wave (for example, indicated by I in FIG. 4 or FIG. 6) and second wave (indicated by II in FIG. 4 or FIG. 6) may be compared.

Further, by calculating the correlative function of standard waveform and diagnostic waveform, the maximum value or pattern may be compared.

Thus, the bone examination method by an ultrasonic wave according to the first aspect of the invention, the comparative items are clear, and the bone properties can be judged easily and accurately.

In the first aspect of the invention, by emitting the ultrasonic wave S into the human bone 3 including spongy bone as the measuring position and penetrating through, the transmitted wave at this time was obtained as a diagnostic wave, and this diagnostic wave was compared with the standard waveform by shape, and the condition of the bone was judged on the basis of presence or absence of difference, but it is also possible to judge the state of the bone by analyzing the propagation waveform in the bone 3 and using quantitative parameters. This method is explained below as a second aspect of the invention.

Figure 22:
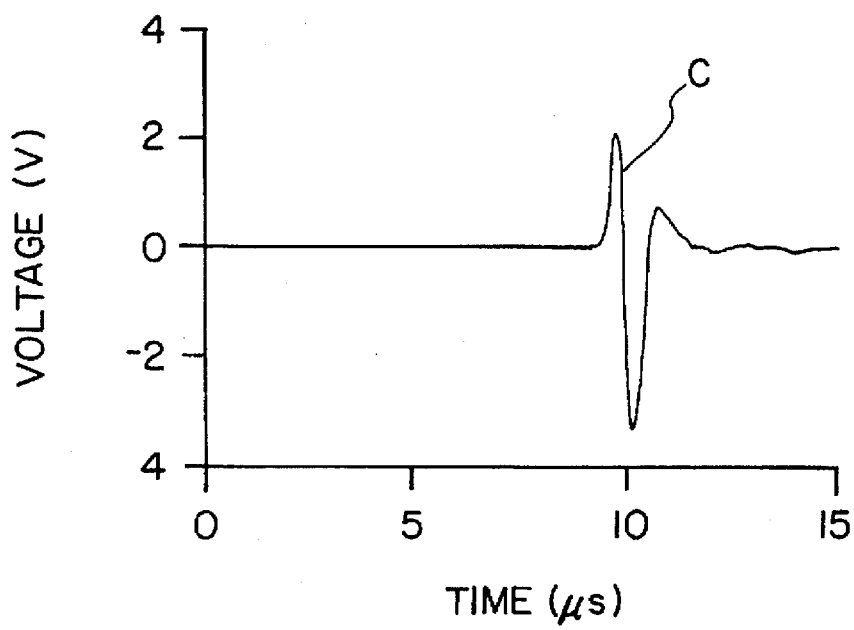
FIG. 22 is a diagram showing an example of an ultrasonic waveform used in a diagnostic method in a second aspect of the invention.

To execute the ultrasonic bone diagnostic method according to the second aspect of the invention, the apparatus shown in FIG. 1 is used. FIG. 22 shows an example of a waveform of ultrasonic wave S used in the diagnostic method of the second aspect of the invention, and waveform c shown in FIG. 22 is generated by applying a voltage of a raised cosine wave.

Figure 23:
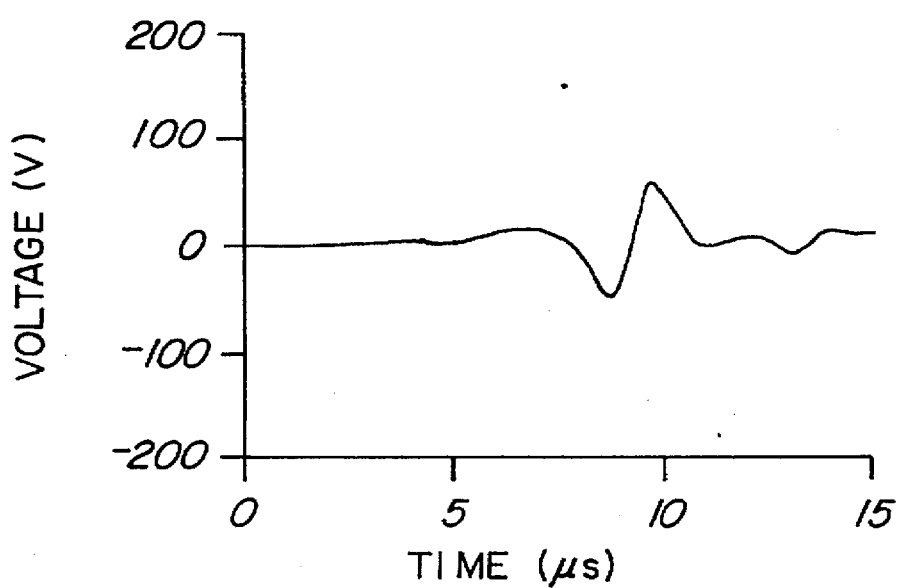
FIG. 23 is a diagram showing an example of a transmitted wave of a healthy subject.
Figure 24:
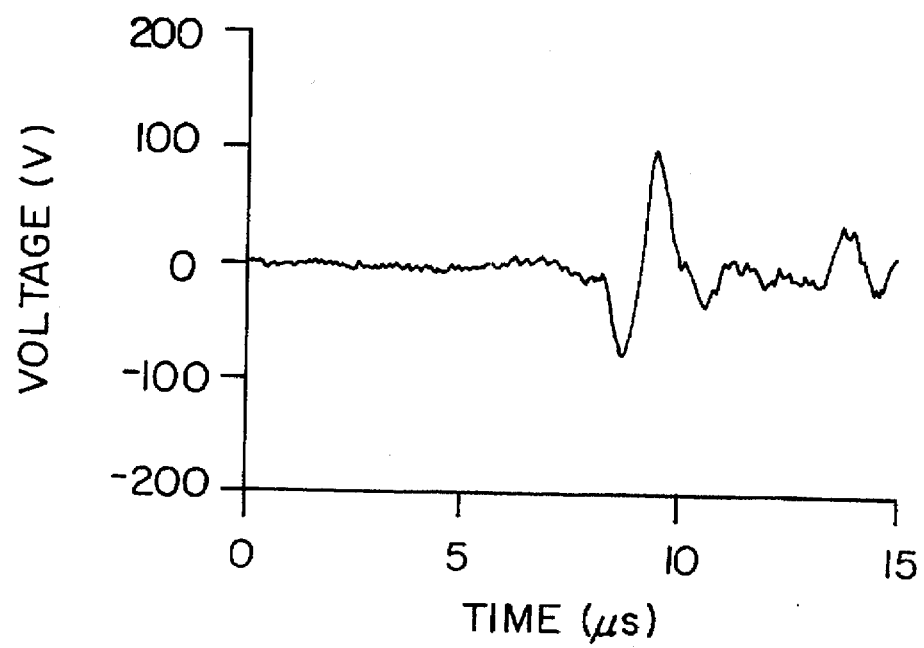
FIG. 24 is a diagram showing an example of a transmitted wave of a patient with light severity.
Figure 25:
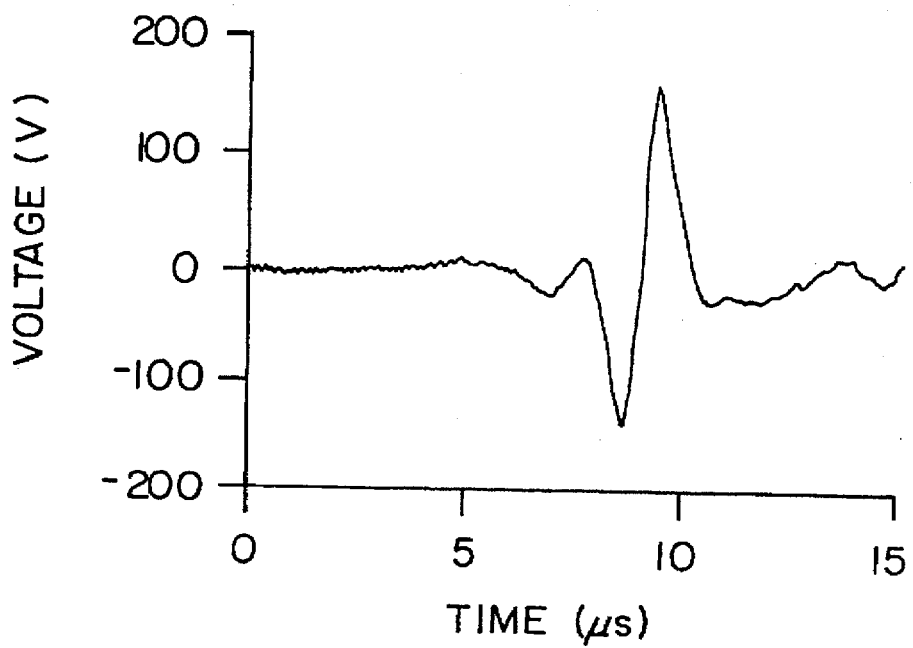
FIG. 25 is a diagram showing an example of a transmitted wave of a patient with heavy severity.

FIGS. 23 to FIG. 25 show waveforms of transmitted waves obtained by emitting the ultrasonic wave S shown in FIG. 22 to the radius 3 of three subjects (healthy subject N, patient with slight osteoporosis X, patient with severe osteoporosis). These subjects N, X, Y were examined separately by the DEXA, and FIG. 23 shows the transmitted wave of the healthy subject N, FIG. 24 shows the transmitted wave of the light severity patient X, and FIG. 25 shows the transmitted wave of the heavy severity patient Y. The transmitted waves are processed by FFT in the computer 6.

Figure 26:
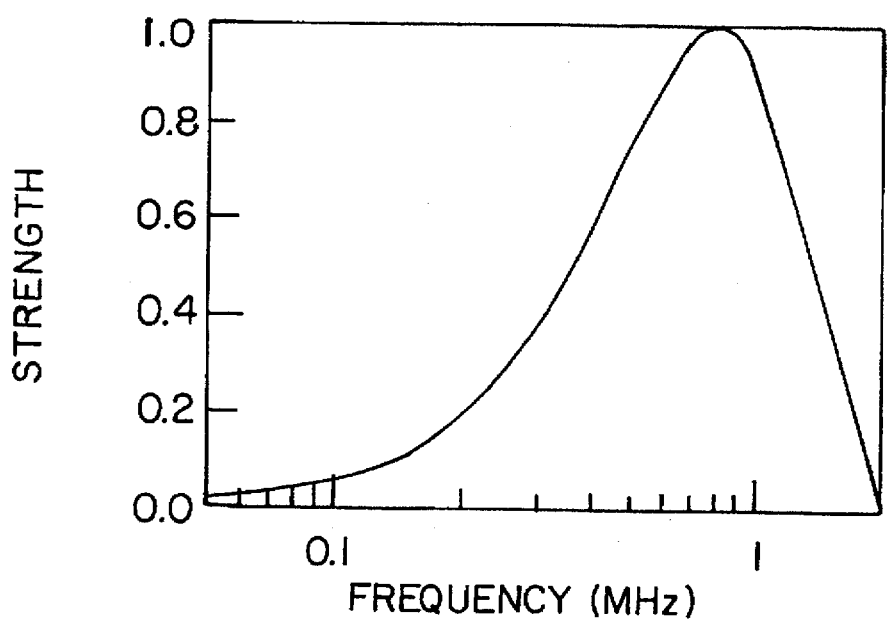
FIG. 26 is a diagram showing an amplitude characteristic of input waveform of ultrasonic wave S.

FIG. 26 shows the frequency characteristic of the input waveform of the ultrasonic wave S used in this measurement, in which the peak is plotted from 100 kHz to 2 MHz, reaching the highest point at about 800 kHz.

Figure 27:
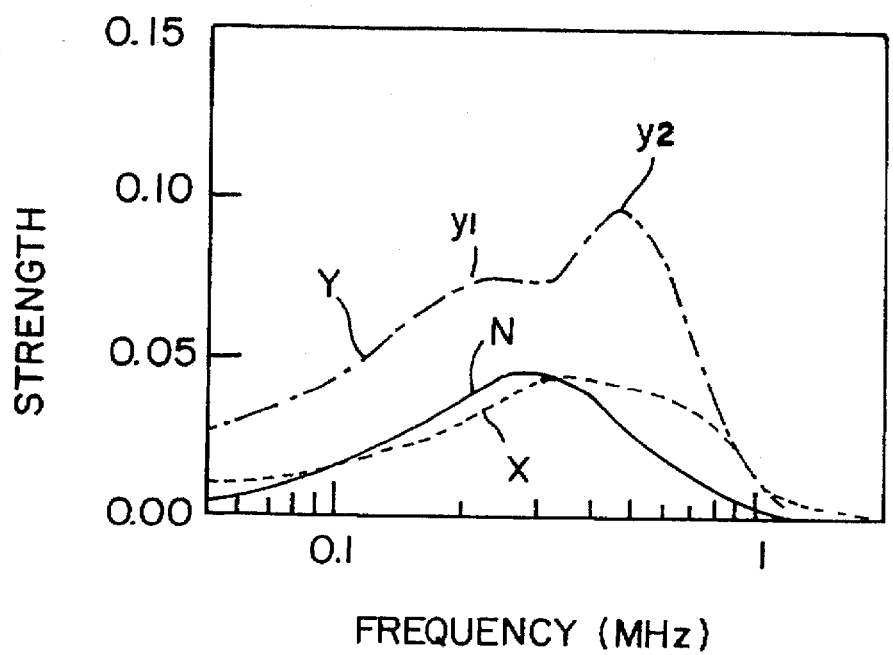
FIG. 27 is a diagram showing a frequency characteristic of amplitude of transmitted wave in each subject.

FIG. 27 shows the frequency characteristic of the waveform propagating through the bone obtained by FFT processing of transmitted waves of the same three subjects, in which symbols N, X, Y in FIG. 27, represent the healthy subject N, light-severity patient X, and heavy severity patient Y respectively. In FIG. 26 and FIG. 27, the axis of abscissas denotes the logarithmic expression of the frequency, and the axis of ordinates represents the strength.

The following is known from FIG. 27. That is, in the characteristic of the healthy subject N, the peak passed the highest point at 300 kHz, and as compared with the characteristic of the input wave shown in FIG. 26, the peak is shifted to the lower frequency side by about 500 kHz, suggesting a large attenuation to the high frequency side around 800 kHz.

In the characteristic of the light-severity patient X, too, the peak was around 300 kHz, and as compared with the characteristic of the input waveform, it is known that the attenuation is significant to the high frequency. On the other hand, it is also known that the attenuation to the high frequency is smaller than that in the healthy subject N.

In the characteristic of the heavy-severity patient Y, on the other hand, there is peak y, around 200 kHz, and another peak $y_2$ has the highest point around 500 kHz. Comparing this characteristic with the characteristic of the input wave, the value is nearly the same as the characteristic of the input wave at less than 100 kHz. At 500 kHz, the attenuation is larger than in the input wave characteristic, but as compared with the characteristic of the light-severity patient X, the transmissivity to the high frequency is obviously higher. As a result, in the characteristic of the heavy-severity patient Y, two peaks y, and Y2 which were hard to detected in that of the healthy subject N can be clearly distinguished (a double-peak curve). Moreover, as a result of analysis of amplitude characteristic and transmission wave frequency of patients with osteoporosis as shown in FIG. 27, it is known that the attenuation of high frequency components tends to be smaller in patients X and Y with osteoporosis than in healthy volunteer N. It is hence possible to set up a diagnostic algorithm of osteoporosis by using the attenuation factor of high frequency components and/or low frequency components as the parameter.

The inventors have already disclosed that the symptoms of osteoporosis causes the transmitted waves to be separated into high speed waves containing many low frequency components, and low speed waves containing many high frequency components in a patent application filed in Japan on Sep. 30, 1993 ("Method and Apparatus of Ultrasonic Bone Diagnosis," Japanese Patent Application 5-270018, Japanese Laid-open Patent Hei. 7-100136), and in consideration of this point, it is estimated that a value around 300 kHz expresses the characteristic of a high speed wave, and that a value around 500 kHz expresses the characteristic of a low speed wave. This patent application also discloses that the amplitude of a low speed wave containing high frequency components increases as the bone density decreases, and in consideration of this point, therefore, the value of the amplitude characteristic of 500 kHz may be regarded as a parameter expressing the bone density.

Figure 28:
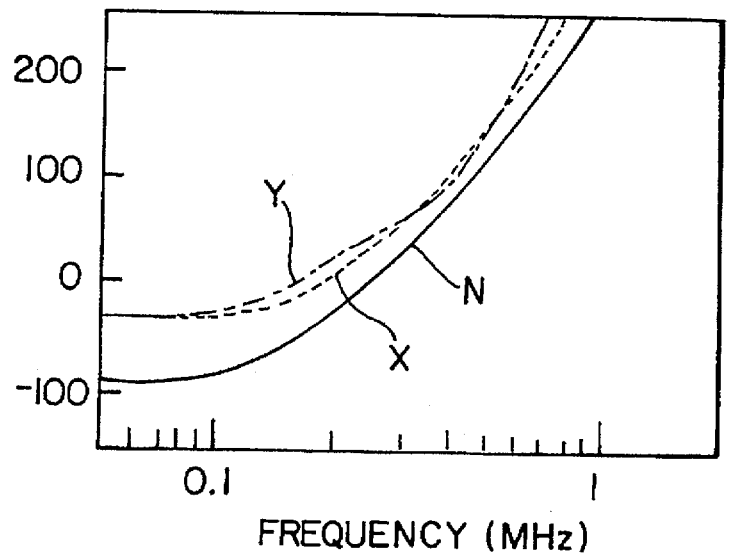
FIG. 28 is a diagram showing a frequency characteristic of phase of transmitted wave in each subject on the basis of incident wave as reference.

Next, on the basis of the phase of input waveform, the frequency characteristic of the phase of the transmitted wave was determined, and the characteristic as shown in FIG. 28 was obtained. In this diagram, the axis of abscissas expresses the frequency logarithmically, and the axis of ordinates indicates the phase relative value.

The following is known from FIG. 28. The characteristic of the healthy subject N is nearly flat at the low frequency side from 100 kHz, and the phase is about −80 degrees. The curve rises sharply after 600 kHz.

On the other hand, the light-severity patient X and heavy-severity patient Y presented similar characteristics, being flat at the low frequency side under 100 kHz, the phase is about −20 degrees, and this value is larger than that of the healthy subject N. At the higher frequency side than 600 kHz, the change is similar to that of the healthy subject N.

That is, the frequency characteristic of phase of the transmitted wave of both patients X and Y is similar to the characteristic of the healthy subject N in the high frequency region, but is smaller than that of the healthy subject N in the low frequency region.

According to the studies by the present inventors, it is found that the transmitted waveform is separated into high speed wave and low speed wave when the bone beam structure is in a unidirectional arrangement, and in consideration of this point, it is estimated that the phase characteristic is changed at low frequency. Incidentally, the phase around 100 kHz may be used as the parameter for expressing the structural change of bone beam.

By utilizing both frequency characteristic of amplitude and frequency characteristic of phase, a technique for measuring the degree of progress of osteoporosis more quantitatively was studied. This is described in detail.

Figure 29:
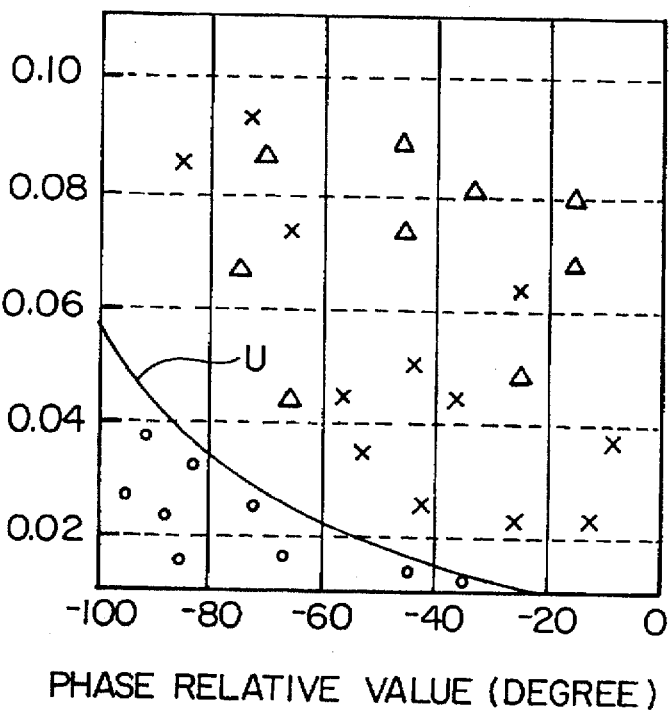
FIG. 29 is a diagram plotting the phase relative value at frequency $\beta$ in the frequency characteristic of phase of transmitted wave in each subject on the axis of abscissas, and the value of frequency characteristic at frequency $\alpha$ in the frequency characteristic of amplitude of transmitted wave in each subject on the axis of ordinates.

The phases of the subjects N, X, Y at frequency β (100 kHz in this example) were particularly marked in difference between the healthy subject N and patients X, Y in the frequency characteristic in phase shown in FIG. 28 from the characteristic values of the subjects N, X, Y at peak frequency α (500 kHz in this example) of the characteristic of the heavy-severity patient Y in the frequency characteristic of amplitude shown in FIG. 27 were expressed in two dimensions, and FIG. 29 was obtained.

The following is known from FIG. 29. The healthy subject N (indicated by circle), and patients X, Y (respectively indicated by x mark and triangle) are plotted at different positions, and when plural samples are plotted each, the distribution is obviously different between the healthy subject N and patients X, Y. In the diagram, the single dot chain line U is a rough boundary of distributions of the healthy subject group and patient group.

In this way, according to the ultrasonic bone diagnostic method of a second aspect of the invention, the state of the human bone can be examined by using quantitative parameters, and the hitherto difficult determination of degree of progress of osteoporosis can be quantitatively judged. In the second aspect of the invention, meanwhile, other frequency analysis than FFT processing may be also employed.

In the first and second aspects of the invention, the frequency of the input ultrasonic wave S is preferred to be 100 kHz to 5 MHz. This is because the difference between the healthy subject and patients is clearly distinguished when the ultrasonic wave S at a frequency in this range is employed. As the ultrasonic wave S, instead of the raised cosine waves, pulse waves containing necessary frequency may be also generated and employed.

As described herein, according to the first and second aspects of the invention, presence or absence of osteoporosis can be judged easily and accurately. It is also possible to predict that the bone structure is simplified. Another possibility is to recognize the structural feature of the bone, and the relation with osteoporosis can be adequately understood.

In particular, according to the second aspect of the invention, the hitherto difficult determination of degree of progress of osteoporosis can be judged quantitatively.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An ultrasonic bone diagnostic method comprising the steps of:

emitting an ultrasonic wave from a transmit transducer to enter and penetrate through a healthy human bone including spongy bone as the measuring position;

receiving the transmitted wave in a receive transducer as a diagnostic waveform;

processing the diagnostic waveform by a computer;

storing the diagnostic waveform as a standard waveform;

emitting an ultrasonic wave from a transmit transducer to enter and penetrate through a subject human bone including spongy bone as the measuring position;

receiving the transmitted wave in a receive transducer as a diagnostic waveform;

processing the diagnostic waveform by a computer; and comparing the diagnostic waveform with a similarly processed prestored standard waveform of a comparably healthy bone, whereby the state of the human bone is judged depending on the presence or absence of difference in the comparison, wherein the comparison step includes comparing the frequency characteristics of the amplitude of the waveform propagating through the human bone as obtained by a Fast Fourier Transformation of the waveform.

2. An ultrasonic bone diagnostic method as set forth in claim 1, in which the waveform processing method by the computer is by frequency analysis.

3. An ultrasonic bone diagnostic method as set forth in claim 2, in which the attenuation factor of high frequency components and/or low frequency components is used as a parameter in the frequency analysis.

4. An ultrasonic bone diagnostic method as set forth in claim 3, in which the attenuation factor of high frequency components and/or low frequency components is used as a parameter for setting up a diagnostic algorithm of osteoporosis.

5. An ultrasonic bone diagnostic method as set forth in claim 2, in which a comparison between the standard waveform and the diagnostic waveform is the frequency characteristic of amplitude of the transmitted wave.

6. An ultrasonic bone diagnostic method as set forth in claim 2, in which a comparison between the standard waveform and diagnostic waveform is the frequency characteristic of the phase of the transmitted wave.

7. An ultrasonic bone diagnostic method as set forth in claim 2, further including the step, wherein the frequency characteristic of the amplitude of the transmitted wave and the frequency characteristic of the phase of the transmitted wave is two-dimensional plotted with phase and amplitude data at a frequency showing a difference between a healthy subject data and unhealthy data.

8. An ultrasonic bone diagnostic method as set forth in claim 1, in which a comparison between the standard waveform and the diagnostic waveform is the frequency characteristic of phase of the transmitted wave.

9. An ultrasonic bone diagnostic method as set forth in claim 1, in which a comparison between the standard waveform and diagnostic waveform is the frequency characteristic of the amplitude of the transmitted wave.

10. An ultrasonic bone diagnostic method as set forth in claim 1, further including the step, wherein the frequency characteristic of the amplitude of the transmitted wave and the frequency characteristic of the phase of the transmitted wave is two-dimensional plotted with phase and amplitude data at a frequency showing a difference between a healthy subject data and unhealthy data.

11. An apparatus for determining an osteoporosis condition of a patient comprising:
    means for applying an ultrasonic wave to a patient's spongy bone;
    means for receiving the ultrasonic wave after it has contacted the patient's bone and generating a representative signal;
    means for storing a comparison signal representative of an equivalent healthy bone; and
    means for comparing the representative signal with the comparison signal to determine the osteoporosis condition including a comparison of an amplitude value relative to phase value of the representative signal and comparison signal.

12. An ultrasonic bone diagnostic method comprising the steps of:
    emitting an ultrasonic wave from a transmit transducer to enter and penetrate through a human bone including spongy bone as the measuring position;
    receiving the transmitted wave in a receiver transducer as a diagnostic waveform;
    comparing the diagnostic waveform with a standard prestored waveform of a comparable healthy bone; and
    judging the state of the human bone depending on the presence or absence of difference from the comparison of one of a zero cross number and pulse width in a range of a time interval including a first wave and a second wave of both waveforms.

13. An ultrasonic bone diagnostic method comprising the steps of:
    emitting an ultrasonic wave from a transmit transducer to enter and penetrate through a human bone including spongy bone as the measuring position;
    receiving the transmitted wave in a receiver transducer as a diagnostic waveform;
    comparing the diagnostic waveform with a standard prestored waveform of a comparable healthy bone; and
    judging the state of the human bone depending on the presence or absence of difference from the comparison of one of one of a magnitude of amplitude of peaks of both waveforms and amplitude ratio of a first wave and a second wave of both waveforms.

14. An ultrasonic bone diagnostic method comprising the steps of:
    emitting an ultrasonic wave from a transmit transducer to enter and penetrate through a human bone including spongy bone as the measuring position;
    receiving the transmitted wave in a receiver transducer as a diagnostic waveform;
    comparing the diagnostic waveform with a standard prestored waveform of a comparable healthy bone; and
    judging the state of the human bone depending on the presence or absence of difference from the comparison of a number of peaks in a range of time interval including a first wave and a second wave of both waveforms.

15. An ultrasonic bone diagnostic method comprising the steps of:
    emitting an ultrasonic wave from a transmit transducer to enter and penetrate through a human bone including spongy bone as the measuring position;
    receiving the transmitted wave in a receiver transducer as a diagnostic waveform;
    comparing the diagnostic waveform with a standard prestored waveform of a comparable healthy bone; and
    judging the state of the human bone depending on the presence or absence of difference from a correlative function between the standard waveform and diagnostic waveform calculated in the comparison step and the judgment step is made from one of a maximum value and a pattern in the correlative function of both waveforms.

16. An ultrasonic bone diagnostic method comprising the steps of:
    emitting an ultrasonic wave from a transmit transducer to enter and penetrate through a healthy human bone including spongy bone as the measuring position;
    receiving the transmitted wave in a receive transducer as a diagnostic waveform;
    processing the diagnostic waveform by a computer;
    storing the diagnostic waveform as a standard waveform;
    emitting an ultrasonic wave from a transmit transducer to enter and penetrate through a subject human bone including spongy bone as the measuring position;
    receiving the transmitted wave in a receive transducer as a diagnostic waveform;
    processing the diagnostic waveform by a computer; and
    comparing the diagnostic waveform with the similarly processed prestored standard waveform of a comparably healthy human bone, whereby the state of the human bone is judged depending on the presence or absence of difference in the comparison, wherein the comparing step includes comparing a frequency characteristic of a phase of a Fast Fourier Transformation of a transmitted wave relative to a phase of an input waveform of a supersonic wave.

17. An ultrasonic bone diagnostic method comprising the steps of:

emitting an ultrasonic wave from a transmit transducer to enter and penetrate through a healthy human bone including spongy bone as the measuring position;

receiving the transmitted wave in a receive transducer as a diagnostic waveform;

processing the diagnostic waveform by a computer;

storing the diagnostic waveform as a standard waveform;

emitting an ultrasonic wave from a transmit transducer to enter and penetrate through a subject human bone including spongy bone as the measuring position;

receiving the transmitted wave in a receive transducer as a diagnostic waveform;

processing the diagnostic waveform by a computer; and comparing the diagnostic waveform with the similarly processed prestored standard waveform of a comparably healthy human bone, whereby the state of the human bone is judged depending on the presence or absence of difference in the comparison, wherein the comparing step is made between a plotted frequency characteristic of an amplitude of a Fast Fourier Transformation of a transmitted wave relative to a plotted frequency characteristic of a phase of a Fast Fourier Transformation of a transmitted wave.

* * * * *